US011654064B2

(12) United States Patent
Corbin et al.

(10) Patent No.: US 11,654,064 B2
(45) Date of Patent: *May 23, 2023

(54) METHOD AND APPARATUS FOR INDICATING CONTINENCE STATE OF A PATIENT ON A BED

(71) Applicant: Hill-Rom Services, Inc., Batesville, IN (US)

(72) Inventors: Scott M. Corbin, Sunman, IN (US); Richard H. Heimbrock, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/713,607

(22) Filed: Apr. 5, 2022

(65) Prior Publication Data

US 2022/0226177 A1    Jul. 21, 2022

Related U.S. Application Data

(63) Continuation of application No. 16/831,926, filed on Mar. 27, 2020, now Pat. No. 11,311,436.

(Continued)

(51) Int. Cl.
*A61G 7/02* (2006.01)
*A61B 5/00* (2006.01)
(Continued)

(52) U.S. Cl.
CPC ............... *A61G 7/02* (2013.01); *A61B 5/002* (2013.01); *A61B 5/202* (2013.01); *A61B 5/6891* (2013.01); *A61B 5/7435* (2013.01); *A61F 13/42* (2013.01); *A61G 7/05* (2013.01); *A61F 2013/422* (2013.01); *A61F 2013/424* (2013.01)

(58) Field of Classification Search
CPC .. A61G 7/02; A61G 7/05; A61B 5/002; A61B 5/202; A61B 5/6891; A61B 5/7435; A61F 13/42; A61F 2013/422; A61F 2013/424
See application file for complete search history.

(56) References Cited

U.S. PATENT DOCUMENTS

| 5,537,095 A | 7/1996 | Dick et al. |
| 6,774,800 B2 | 8/2004 | Friedman et al. |

(Continued)

FOREIGN PATENT DOCUMENTS

WO    2015/137999    9/2015

OTHER PUBLICATIONS

European Communication under Rule 71(3) EPC from European Patent Application No. 20166516.3 dated Mar. 17, 2022, 48 pages.

(Continued)

*Primary Examiner* — Nabil H Syed
*Assistant Examiner* — Cal J Eustaquio
(74) *Attorney, Agent, or Firm* — Barnes & Thornburg LLP

(57) ABSTRACT

A patient support apparatus includes a frame and a mattress supported by the frame and arranged to support a patient thereon. A sensor is included to detect moisture on the patient and/or the patient support apparatus. The sensor produces signals indicative of the presence of moisture on the patient support apparatus. One or more alerts are output in response to the signals provided by the sensor to notify a caregiver of the presence of moisture on the patient support apparatus.

20 Claims, 7 Drawing Sheets

Related U.S. Application Data

(60) Provisional application No. 62/833,040, filed on Apr. 12, 2019.

(51) Int. Cl.
  *A61B 5/20* (2006.01)
  *A61F 13/42* (2006.01)
  *A61G 7/05* (2006.01)

(56) References Cited

U.S. PATENT DOCUMENTS

| | | |
|---|---|---|
| 9,655,798 B2 | 5/2017 | Zerhusen et al. |
| 10,022,277 B2 | 7/2018 | Heil et al. |
| 10,115,291 B2 | 10/2018 | Tallent et al. |
| 10,159,607 B2 | 12/2018 | Monson et al. |
| 10,299,968 B2 | 5/2019 | Heil et al. |
| 10,470,689 B2 | 11/2019 | Kileran et al. |
| 10,500,105 B2 | 12/2019 | Monson et al. |
| 10,517,784 B2 | 12/2019 | Zerhusen et al. |
| 10,624,804 B2 | 4/2020 | Williams et al. |
| 10,646,379 B2 | 5/2020 | Heil et al. |
| 10,653,567 B2 | 5/2020 | Weidman et al. |
| 2002/0014951 A1 | 2/2002 | Kramer et al. |
| 2002/0145526 A1 | 10/2002 | Friedman et al. |
| 2005/0242946 A1 | 11/2005 | Hubbard et al. |
| 2011/0133935 A1 | 6/2011 | Beltmann et al. |
| 2013/0194373 A1 | 8/2013 | Roberts et al. |
| 2014/0276504 A1 | 9/2014 | Heil et al. |
| 2017/0065464 A1 | 3/2017 | Heil et al. |
| 2018/0021184 A1 | 1/2018 | Monson et al. |
| 2018/0184984 A1 | 7/2018 | Zerhusen |
| 2019/0051137 A1 | 2/2019 | Kilcran et al. |
| 2019/0060137 A1 | 2/2019 | Severns et al. |

OTHER PUBLICATIONS

European Communication pursuant to Article 94(3) EPC from European Patent Application No. 20166516.3 dated May 17, 2021, 7 pages.

Extended European Search Report for European Patent Application No. 20166516.3 dated Aug. 20, 2020 (9 pages).

First Office Action with English Translation for Chinese Patent Application No. 202010256875.3, dated Jun. 22, 2021, (32 pages).

European Search Report for EP 22187340.9 dated Feb. 12, 2022.

METHOD AND APPARATUS FOR INDICATING CONTINENCE STATE OF A PATIENT ON A BED

CROSS-REFERENCE TO RELATED APPLICATIONS

This application is a continuation of U.S. patent application Ser. No. 16/831,926, filed Mar. 27, 2020, which claims the benefit, under 35 U.S.C. § 119(e), to U.S. Provisional Application No. 62/833,040, filed Apr. 12, 2019, the contents of each of which is incorporated by reference in its entirety into the present application.

BACKGROUND

The present disclosure relates to patient support apparatuses having alerting capabilities. More specifically, the present disclosure relates to patient support apparatuses that include sensors for monitoring an incontinence state of a patient and structures for alerting caregivers when moisture is detected.

Patients in healthcare facilities may become incontinent and may need the wetness to be removed from the bed to prevent undesirable side effects. When moisture is detected by an incontinence detection system, a nurse may receive an alert of the incontinence state immediately, although immediate action may not be needed nor possible if all nurses are preoccupied with other, urgent tasks. Furthermore, other members in the vicinity of the patient and the hospital bed may become upset if they notice an alert that the patient has become incontinent yet no caregivers are available to immediately assist them.

SUMMARY

The present application discloses one or more of the features recited in the appended claims and/or the following features which, alone or in any combination, may comprise patentable subject matter:

In a first aspect of the present disclosure, a patient support apparatus includes a frame, an incontinence detection pad supported by the frame, and an indicator. The incontinence detection pad is operable to detect incontinence of a patient supported by the frame. The indicator is coupled to the frame and operable to provide a visual indication that incontinence has been detected by the incontinence detection pad.

In some embodiments, a user input is provided to enable and disable the indicator. When the indicator is disabled, no visual indication that incontinence has been detected by the incontinence detection pad is provided by the indicator.

In some embodiments, the indicator includes a light at a foot end of the frame. The visual indication includes an incontinence icon that is projected onto a floor adjacent to the frame.

In some embodiments, the patient support apparatus further includes communication circuitry coupled to the frame and operable to transmit an incontinence status signal for receipt by a remote computer. The patient support apparatus further includes a graphical user interface (GUI) coupled to the frame and wherein the user input is displayed on the GUI.

In some embodiments, the incontinence detection pad provides a wireless signal indicative of an incontinence detection state. The indicator comprises a light coupled to the frame and a projector coupled to the frame and operable to project an incontinence icon onto a surface adjacent the frame. The light includes a second incontinence icon that matches an appearance of the incontinence icon that is projected onto the surface. The user input is usable to enable and disable the light, the projector, or both.

According to another aspect of the present disclosure, a system includes a patient support apparatus, and a detection and notification system. The detection and notification system includes an incontinence detection pad, an external alarm system, and a controller. The incontinence detection pad is supported by the patient support apparatus and having a condition-responsive sensor to produce a signal indicative of moisture being present on the incontinence detection pad. The external alarm system includes a first indicator located in the vicinity of the incontinence detection pad and a second indicator located in a remote location out of view from the incontinence detection pad In some embodiments, the first and second indicators display a first iconic representation indicative of a lack of moisture on the incontinence detection pad and a second iconic representation indicative of the presence of moisture on the incontinence detection pad. The controller is coupled to the incontinence detection pad and includes a processor and a memory device storing instructions that, when executed, cause the first indicator to display selectively the first iconic representation when the condition-responsive sensor produces the signals and the second indicator to display the second iconic representation when the condition-responsive sensor produces the signals.

In some embodiments, the controller is reprogrammable through user inputs to display selectively the first or the second iconic representation using the first indicator when the condition-responsive sensor determines that moisture is present on the incontinence detection pad. The first iconic representation includes an iconic representation with a first color and the second iconic representation includes the iconic representation with a second color different from the first color to indicate the presence of moisture on the incontinence detection pad.

In some embodiments, the first indicator includes an indicator panel coupled to the patient support apparatus. The first indicator may be coupled to a foot end of the frame. The first indicator further may include a projector configured to display an image on a surface spaced apart from the patient support apparatus. The surface includes a floor around the patient support apparatus. The first and second iconic representations may be displayed at the same time.

In some embodiments, the system further includes a user interface for receiving user inputs to control the first indicator to cause the first indicator to display selectively the first iconic representation or the second iconic representation. The user interface includes a touch screen with a number of button icons for receiving user inputs to control the first indicator to cause the first indicator to display selectively the first iconic representation or the second iconic representation.

In some embodiments, the button icons include a first indicator button icon that, when selected, may cause the first indicator to turn off such that the first and second iconic representations are displayed only by the second indicator. The button icons include a second indicator button icon that, when selected, may cause the indicator panel and the projector to display both the first and second iconic representations such that the first and second iconic representations are displayed by both the first the second indicators. The button icons include a projector button icon that, when selected, may cause the projector to turn off such that the first and second iconic representations are displayed only by the indicator panel and the second visual indicator.

According to another aspect of the present disclosure, a method includes: providing a patient support apparatus with a detection and notification system including a first indicator in a proximate location to the patient support apparatus and a second indicator in a remote location to the patient support apparatus. The method further includes displaying a first iconic representation at the proximate location when a condition is lacking. The method further includes displaying the first iconic representation at the remote location when the condition is lacking.

In some embodiments the method further includes displaying a second iconic representation at the remote location when the condition is present and displaying selectively the first iconic representation at the proximate location when the condition is present. The condition is the presence of moisture on the patient support apparatus detected by a sensor.

According to another aspect of the present disclosure, a detection and notification system includes a condition-responsive sensor to produce a signal indicative of moisture being present, an external alarm system, and a controller. The external alarm system includes a first indicator located in a proximate location to the sensor and a second indicator located in a remote location out of view from the sensor. The controller coupled to the sensor to receive the signal produced by the sensor.

In some embodiments, the first and second indicators display a first iconic representation indicative of a lack of moisture and a second iconic representation indicative of the presence of moisture. The controller includes a processor and a memory device storing instructions that, when executed, cause the first indicator to display selectively the first iconic representation or the second iconic representation when the condition-responsive sensor produces the signals and the second indicator to display the second iconic representation when the condition-responsive sensor produces the signals.

According to another aspect of the present disclosure, a detection and notification system includes an incontinence detection pad having a condition-responsive sensor to produce a signal indicative of moisture being present on the incontinence detection pad, an external alarm system, and a controller. The external alarm system includes a first indicator located in a proximate location to the incontinence detection pad and a second indicator located in a remote location out of view from the incontinence detection pad. The controller is coupled to the incontinence detection pad and the external alarm system.

In some embodiments, the controller includes a processor and a memory device storing instructions that, when executed, cause the first indicator to display selectively a first iconic representation or a second iconic representation when the condition-responsive sensor produces the signals and the second indicator to display the second iconic representation when the condition-responsive sensor produces the signals. The first indicator displays the first iconic representation when the incontinence detection pad is installed on the patient support apparatus, the second iconic representation displays the first indication when there is a lack of moisture on the incontinence detection pad, and the second indicator displays the second iconic representation when there is a presence of moisture on the incontinence detection pad. The first visual indicator continues to display the first iconic representation when there is a presence of moisture on the incontinence detection pad.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which:

FIG. 2 is a screen shot of a home screen displayed on the graphical user interface in accordance with the present disclosure;

FIG. 3 is a screen shot of a settings screen displayed on the graphical user interface in accordance with the present disclosure;

FIG. 4 is a screen shot of a bed features screen displayed on the graphical user interface in accordance with the present disclosure;

FIG. 5 is a screen shot of an indicator settings screen displayed on the graphical user interface in accordance with the present disclosure;

FIG. 6 is a screen shot of an incontinence indicator screen displayed on the graphical user interface in accordance with the present disclosure; and FIG. 7 is a screen shot of a projector screen displayed on the graphical user interface in accordance with the present disclosure.

DETAILED DESCRIPTION

Figure 1:
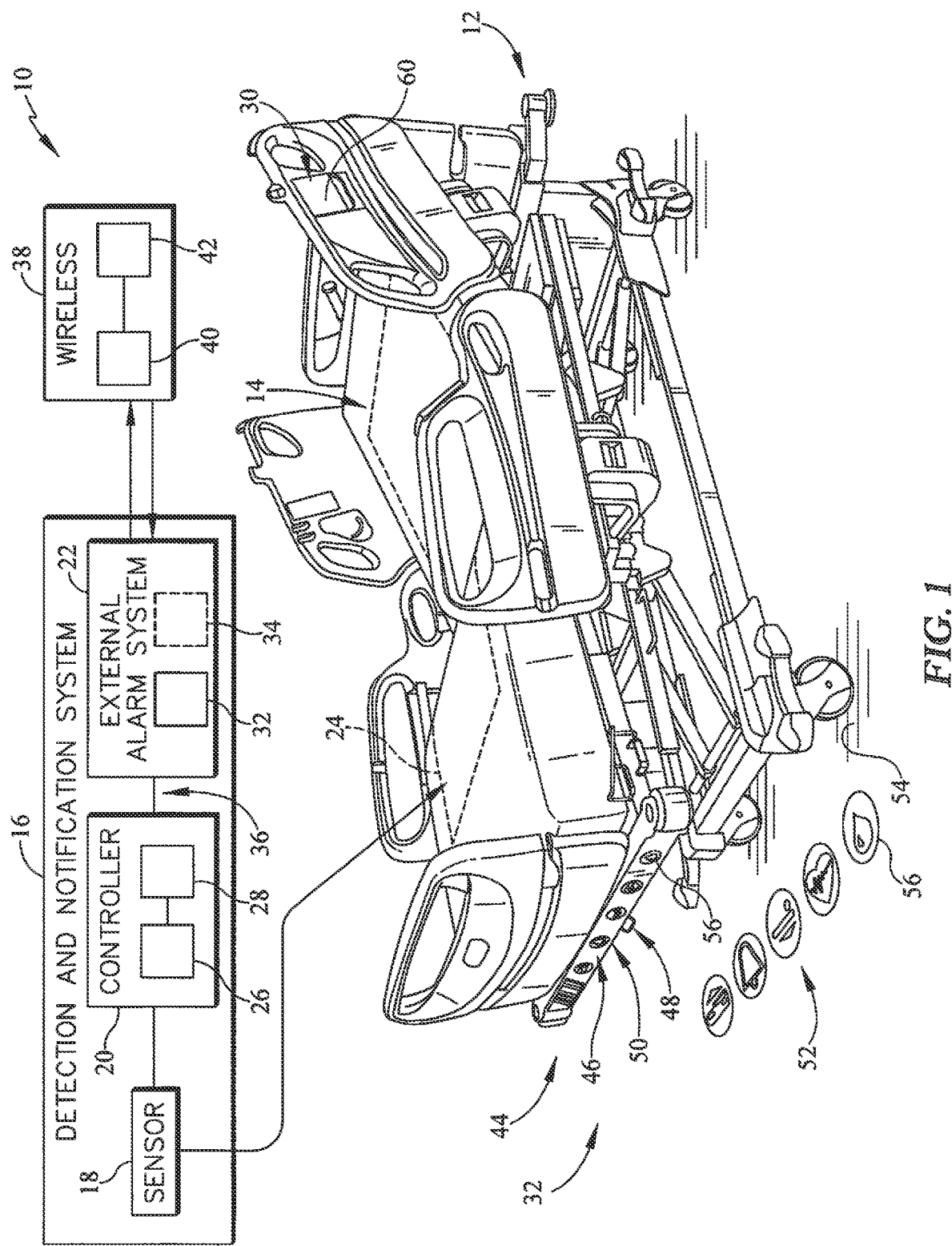
FIG. 1 is a perspective view of a patient support apparatus including a detection and notification system according to the present disclosure and a user interface with a touch screen used to control the detection and notification system.
Figure 2:
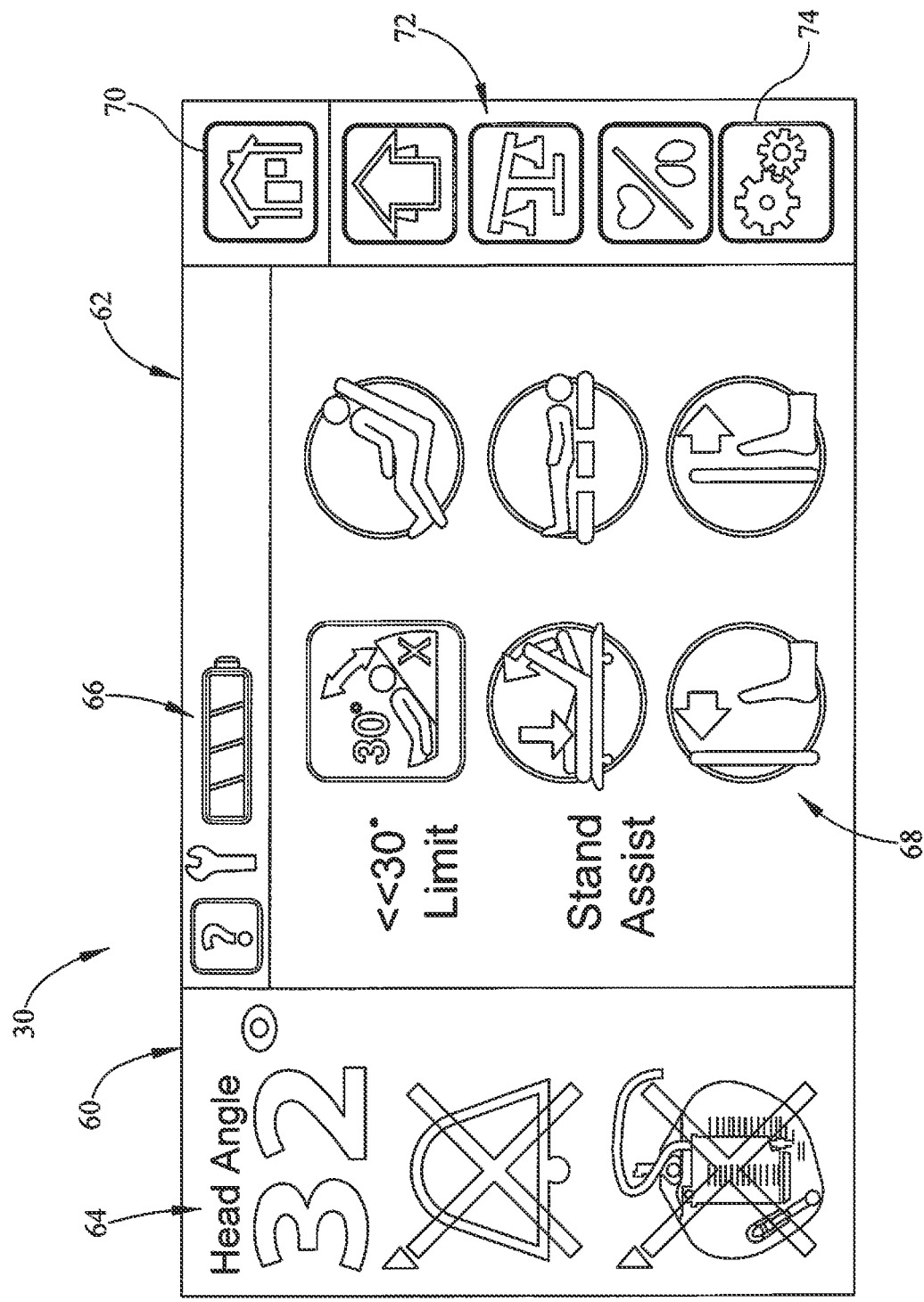
FIG. 2-7 are diagrammatic representations displayed on the graphical user interface with a number of button icons for controlling the detection and notification system.

Referring to FIG. 1, a patient support apparatus 10 is illustratively embodied as a hospital bed 10. The hospital bed 10 includes a frame 12, a mattress 14 supported on the frame 12, and a detection and notification system 16. An example of a suitable frame 12 and mattress 14 is shown and described in U.S. Patent Pub. No. 2018/0184984 which is expressly incorporated by reference herein for the purpose of describing the frame 12 and mattress 14 along with associated functions and capabilities of the frame 12 and mattress 14. The detection and notification system 16 is configured to determine an incontinence state of a patient resting on the mattress 14 and display selectively notifications that indicate various statuses of the detection and notification system 16.

The detection and notification system includes a condition-responsive sensor 18, a controller 20 coupled to the sensor 18, and an external alarm system 22 as shown diagrammatically in FIG. 1. The sensor 18 is configured to sense the presence of moisture on the patient and/or the mattress 14 and output signals indicative thereof. The controller 20 receives the signals from the sensor 18 and issues commands to the external alarm system 22 to provide a notification based on user inputs and/or user preferences stored in the controller 20. The external alarm system 22 provides one or more notifications that match the stored inputs or preferences.

In the illustrative embodiment, the sensor 18 is integrated into an incontinence detection pad 24 that is supported on the mattress 14 and the frame 12 as suggested in FIG. 1. The incontinence detection pad 24 is positioned on the hospital bed 10 for surveillance for unwanted incontinence fluids or other biofluids that may be produced by a patient. The incontinence detection pad 24 absorbs and retains the fluids therein and the incontinence detection pad 24 may be removed and replaced without replacing the entire mattress 14. An example of a suitable incontinence detection pad 24 is shown and described in U.S. Patent Pub. No. 2019/0060137 which is expressly incorporated by reference herein for the purpose of describing a suitable incontinence detection pad.

The condition-responsive sensor 18 includes a sensor circuit with a plurality of electrically conductive traces printed on a substrate of the incontinence detection pad 24 that produce the sensor signals when moisture is present on the incontinence detection pad 24. Examples of a suitable sensor with a sensor circuit integrated into an incontinence detection pad is shown and described in U.S. Patent Pub. Nos. 2017/0065464 and 2018/0021184, each of which is expressly incorporated herein for the purpose of showing and describing a suitable sensor for an incontinence detection pad and means for powering the sensor and transmitting the signals produced by the sensor. In some embodiments, the sensor 18 communicated wirelessly with controller 20. In other embodiments, a wired connection is provided between sensor 18 and controller 20.

The controller 20 includes a processor 26 and a memory device 28 storing instructions that, when executed, cause the external alarm system 22 to display selectively the notifications according to the user inputs. The controller 20 includes all of the functionality needed to operate the external alarm system 22 and is coupled with a graphical user interface 30 mounted on or near the hospital bed 10 as shown in FIG. 1. The user inputs are entered by a caregiver with the graphical user interface 30 and are stored in memory device 28 to program the controller 20 to operate the external alarm system 22 according to the caregiver's and/or patient's preferences.

The external alarm system 22 displays notifications that represent statuses of the sensor 18 based on the user inputs that have been entered into the user interface 30 and stored in the memory device 28 of the controller 20. In one embodiment, the status of the sensor 18 is whether or not moisture is present on the incontinence detection pad 24. In another embodiment, the status of the sensor 18 is whether or not the hospital bed 10 is provided with an incontinence fluid sensing capability (i.e. the incontinence detection pad 24 with the integrated sensor 18).

The external alarm system 22 includes a first indicator 32 located in a proximate location to the hospital bed 10 and a second indicator 34 located in a remote location out of view from the hospital bed 10. The proximate location may be in the same room as the hospital bed 10 while the remote location is outside of the room with the hospital bed 10. The controller 20 may be coupled with the external alarm system 22 through a suitable connection, such as a universal asynchronous receiver/transmitter (UART) connection 36, or through a wireless connection 38 that includes one or more antennas 40 and/or transceivers 42. The first indicator 32 displays iconic representations on or near the hospital bed 10. Depending on the user inputs entered into the user interface 30, the first indicator 32 may display an iconic representation indicative of whether or not moisture is present on incontinence detection pad 24, or an iconic representation indicative of whether or not the patient's hospital bed 10 is currently provided with an incontinence detection pad 24. The second indicator 34 may display the same representations at the remote location or different representations depending on the user inputs entered into the user interface 30. In the illustrative embodiment, the second indicator 34 is located at a master nurse call station.

When a status of the sensor 18 changes, the first and the second indicators may display a new iconic representation to alert the caregiver of the change and indicate that appropriate action may be needed such as, for example, changing a wet or soiled incontinence detection pad 24. In some instances, changing a wet or soiled incontinence detection pad is not an action that requires urgent completion and medical personnel made be delayed in responding to the action if they are busy with other patients. Still, the sensor 18 within the incontinence detection pad 24 is configured to provide the signals as soon as moisture is detected on the incontinence detection pad 24. Upon receiving the signals from the sensor 18, the controller 20 may cause the first indicator 32 to display the new iconic representation proximate to the hospital bed 10 as soon as the sensor 18 detects the moisture. Non-medical personnel within the room may see the new iconic representation and expect urgent action to remedy the situation even though urgent action may not be needed and/or possible at that time. Accordingly, the non-medical personnel may become irritated or upset that the patient's incontinence detection pad 24 has not been changed. The external alarm system 22 in the illustrative embodiment may be programmed selectively through the user inputs into the user interface 30 to either: 1) turn off the first indicator 32 such that only the second indicator 34 is used; 2) display an iconic representation with the first indicator 32 that indicates only that the hospital bed 10 is currently provided with an incontinence detection pad 24; or 3) change selectively what types of indications are provided by the first indicator 32.

In the illustrative embodiment, the first indicator 32 is mounted to a foot end 44 of the hospital bed 10 and includes an indicator panel 46 and a projector 48 as shown in FIG. 1. The indicator panel 46 displays a plurality of iconic representations 50 associated with different features of the hospital bed 10 and/or information related to the patient. The projector 48 illuminates iconic representations 52 on a surface 54 that is spaced apart from the hospital bed 10. The iconic representations 52 illuminated by the projector 48 are substantially similar to the iconic representations 50 displayed by the indicator panel 46; however, in other embodiments, they may be different. In the illustrative embodiment, the surface 54 is the floor near the foot end 44 of the hospital bed 10; however, the surface 54 may be a wall or another surface located proximate to the hospital bed 10. An example of a suitable indicator panel and projector is described in U.S. Patent Pub. No. 2018/0184984, which is already incorporated by reference herein and may also be used for the purpose of describing a suitable indicator panel capable of displaying the iconic representations and a suitable projector capable of illuminating the iconic representations.

In the illustrative embodiment, one such iconic representation displayed by the indicator panel 46 and illuminated by the projector 48 is a water droplet 56 as shown in FIG. 1. The water droplet 56 is associated with the sensor 18 in the incontinence detection pad 24. The controller 20 displays the water droplet 56 on the indicator panel 46 and/or illuminates the water droplet using the projector depending on the user inputs entered into the user interface 30. In one embodiment, the controller 20 causes the water droplet 56 to change colors as the status of the sensor 18 in the incontinence detection pad 24 changes. In the illustrative embodiment, the controller 20 causes first indicator to display and/or illuminate the water droplet 56 with a white color when the hospital bed 10 is not provided with an incontinence detection pad 24. The controller 20 causes the first indicator 32 to display and/or illuminate the water droplet 56 with a green color when an incontinence detection pad 24 is provided in the hospital bed 10. In other embodiments, other colors may be used to indicate the presence or lack of an incontinence detection pad 24 on the hospital bed 10.

In one embodiment, the green color indicates a lack of moisture on the incontinence detection pad 24 as determined by the sensor 18. Once the sensor 18 detects moisture on the incontinence detection pad 24, a signal is output to the controller 20 and the controller 20, upon receipt of the signal, causes the first indicator 32 to display and/or illuminate the water droplet 56 with an amber color to notify a caregiver that action is needed. In other embodiments, any suitable color may be used to indicate the presence of moisture on the incontinence detection pad 24 and that action is needed. The controller 20 also causes the second indicator 34 to notify the caregiver at the remote location that action is needed. The second indicator 34 may display and/or illuminate a similar iconic representation to the water droplet 56 in a similar manner to first indicator 32; however, any suitable method of notifying a caregiver at the remote location may be used.

In accordance with the present disclosure, the user interface 30 receives user inputs that selectively change an appearance of the iconic representations 50, 52 at the proximate location than the appearance typically displayed and/or illuminate when the sensor 18 detects moisture on the incontinence detection pad 24. In one embodiment, the user inputs program the controller 20 to cause the first indicator 32 to continue to display and/or illuminate the water droplet 56 with the green color even when moisture is present on the incontinence detection pad 24. In this instance, the green color indicates only that the hospital bed 10 has been provided with an incontinence detection pad 24. In another embodiment, the indicator panel 46 and/or the projector 48 of the first indicator 32 may be turned off such that only the second indicator 34 notifies a caregiver at the remote location when moisture is detected on the incontinence detection pad 24 by the sensor 18.

Referring now to FIGS. 2-7, the graphical user interface 30 displays a touchscreen 60 that includes a number of icons which may be selected by a user to control various functions of the hospital bed 10. The functionality of the touchscreen 60 is disclosed in the PCT application WO2016/196403, filed May 29, 2016, and incorporated by reference herein for the disclosure of a touch screen menu structure of the hospital bed 10. The touchscreen 60 displays a home screen 62 that includes an alarm status section 64, an information bar 66, a function panel 68, a home key 70, and a scrolling menu 72. The scrolling menu 72 includes a settings button icon 74 which, when touched by a user, activates a settings screen 76 shown in FIG. 3.

Figure 3:
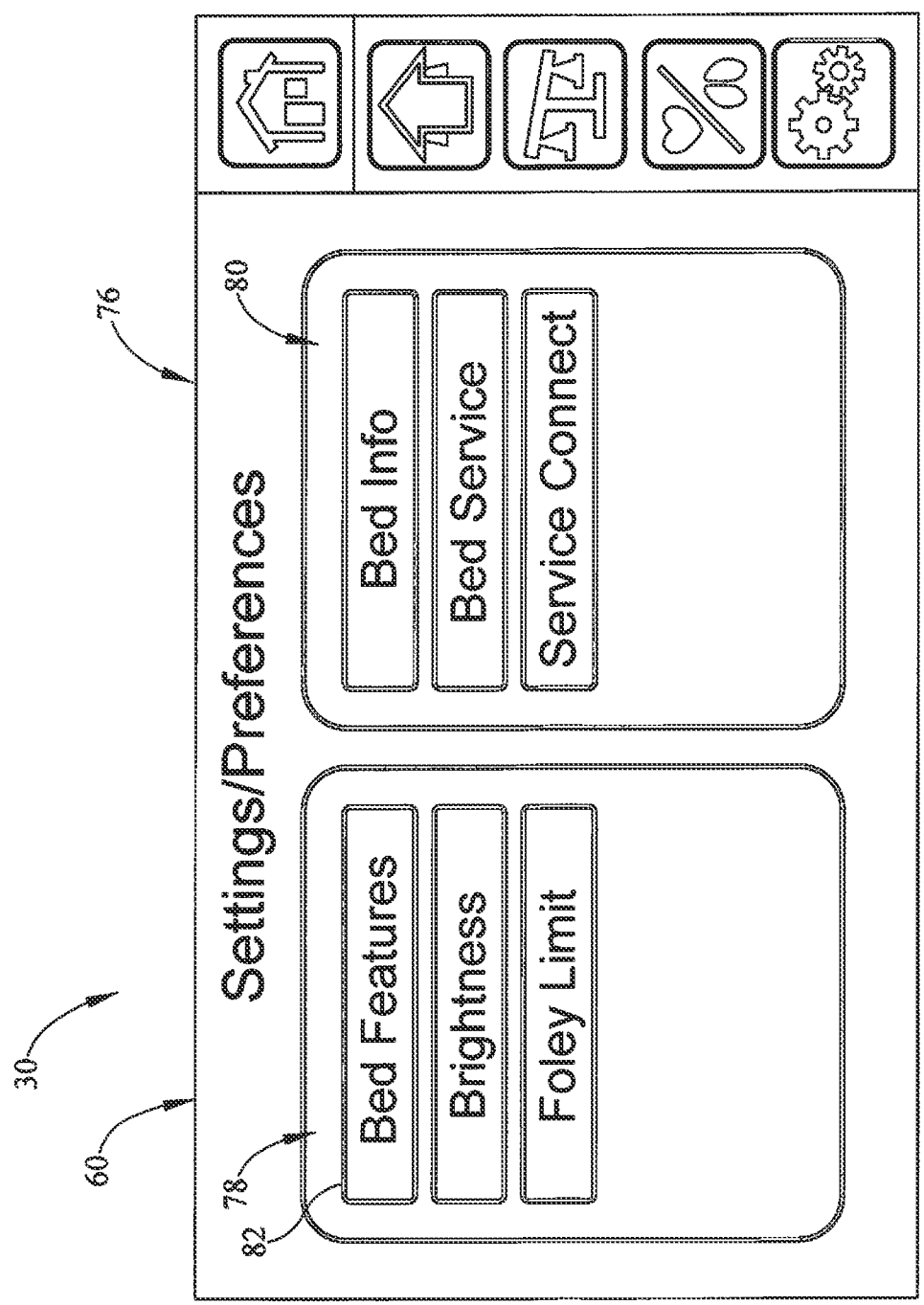

The settings screen 76 is displayed on the graphical user interface 30 when the settings button icon 74 is touched as shown in FIG. 3. The settings screen 76 includes a bed function panel 78 and a bed information panel 80. The bed function panel 78 includes a bed features button icon 82 which, when touched by the user, activates a bed features screen 84 as shown in FIG. 4.

Figure 4:
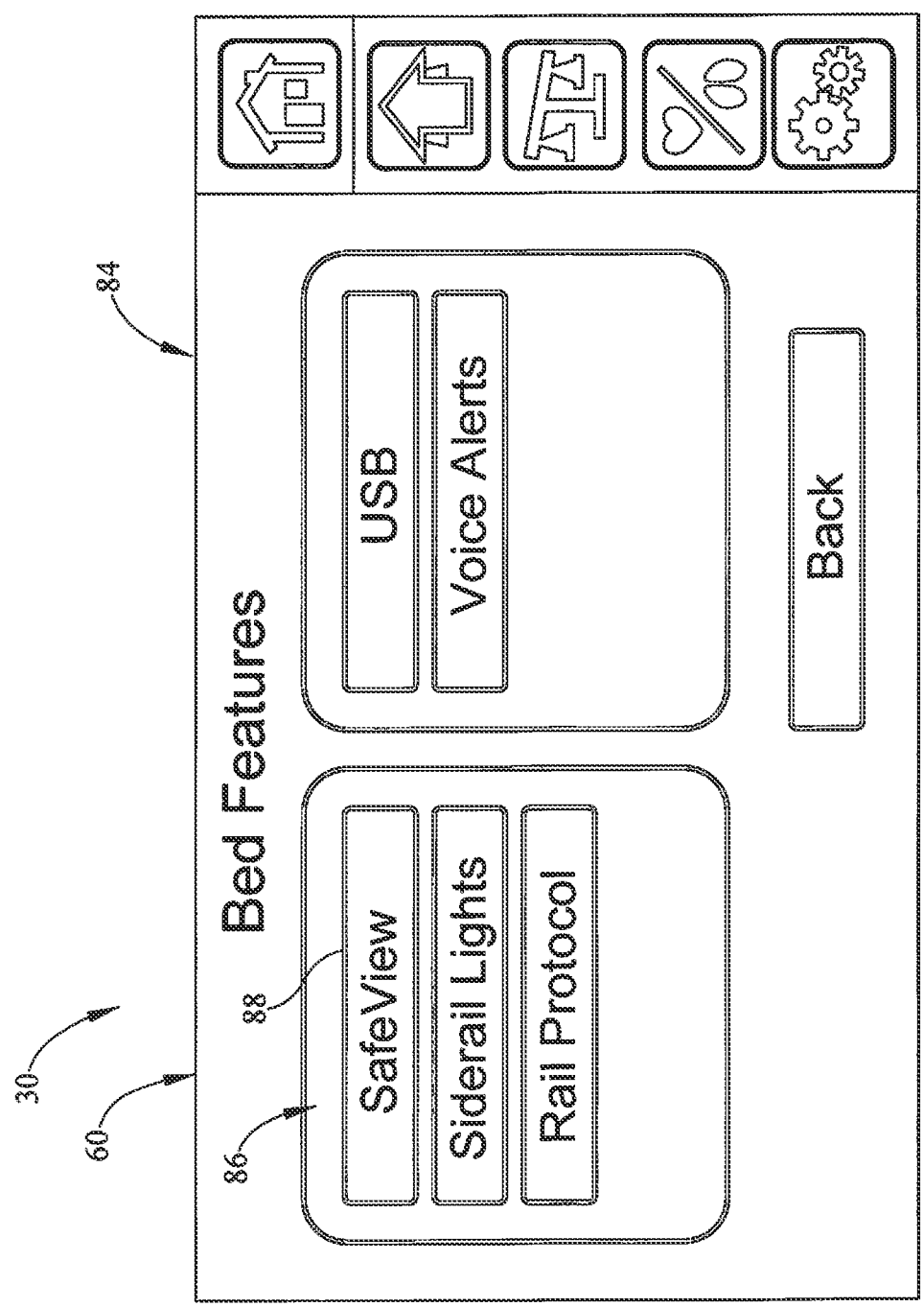
Figure 5:
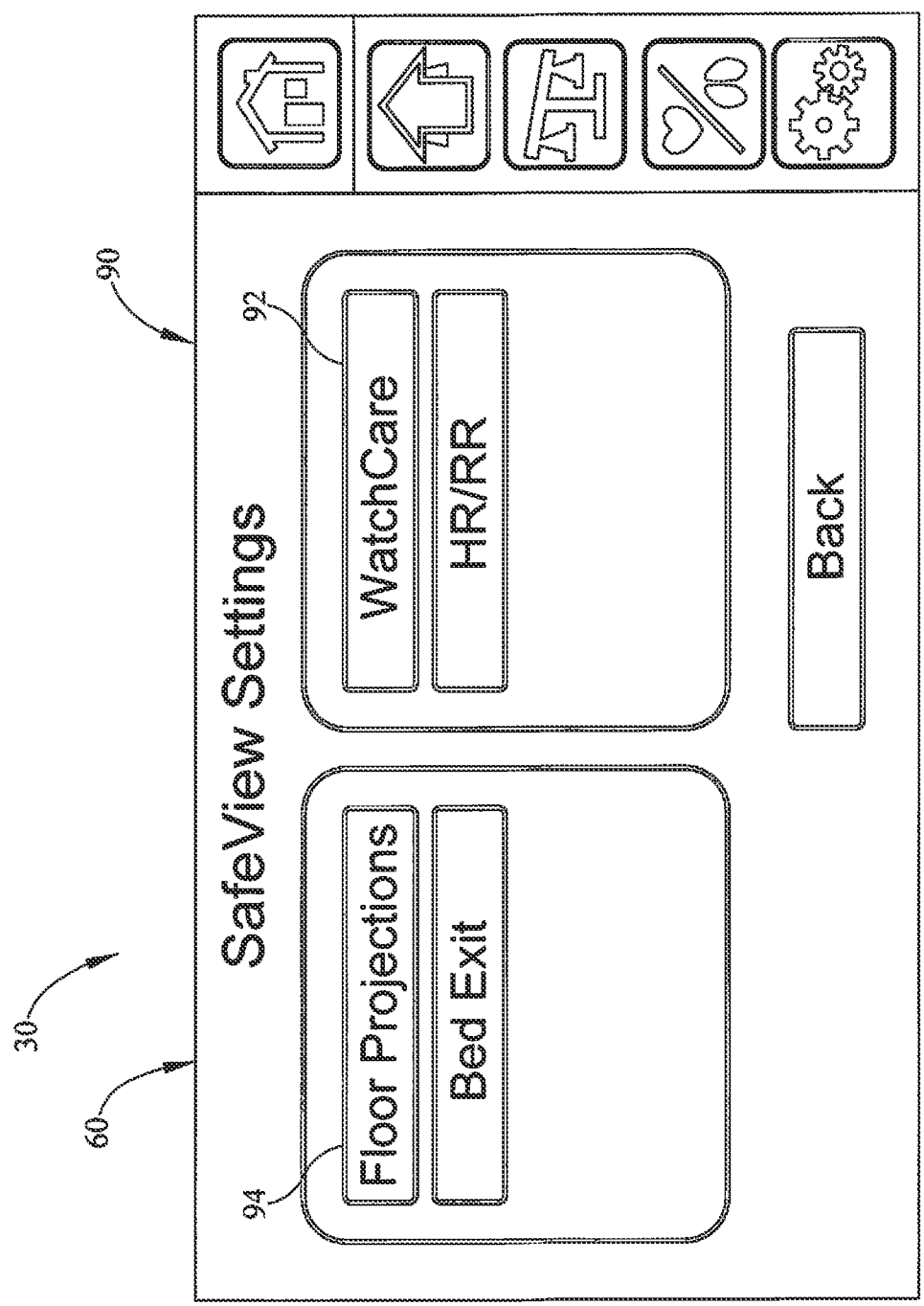

The bed features screen 84 includes a display function panel 86 as shown in FIG. 4. The display function panel 86 includes a selection button icon 88 which, when touched by the user, activates an indicator settings screen 90 as shown in FIG. 5. The selection button icon 88 depicts SAFE-VIEW™, which is a proprietary term that is used to represent various functions associated with the detection and notification system 16.

Figure 6:
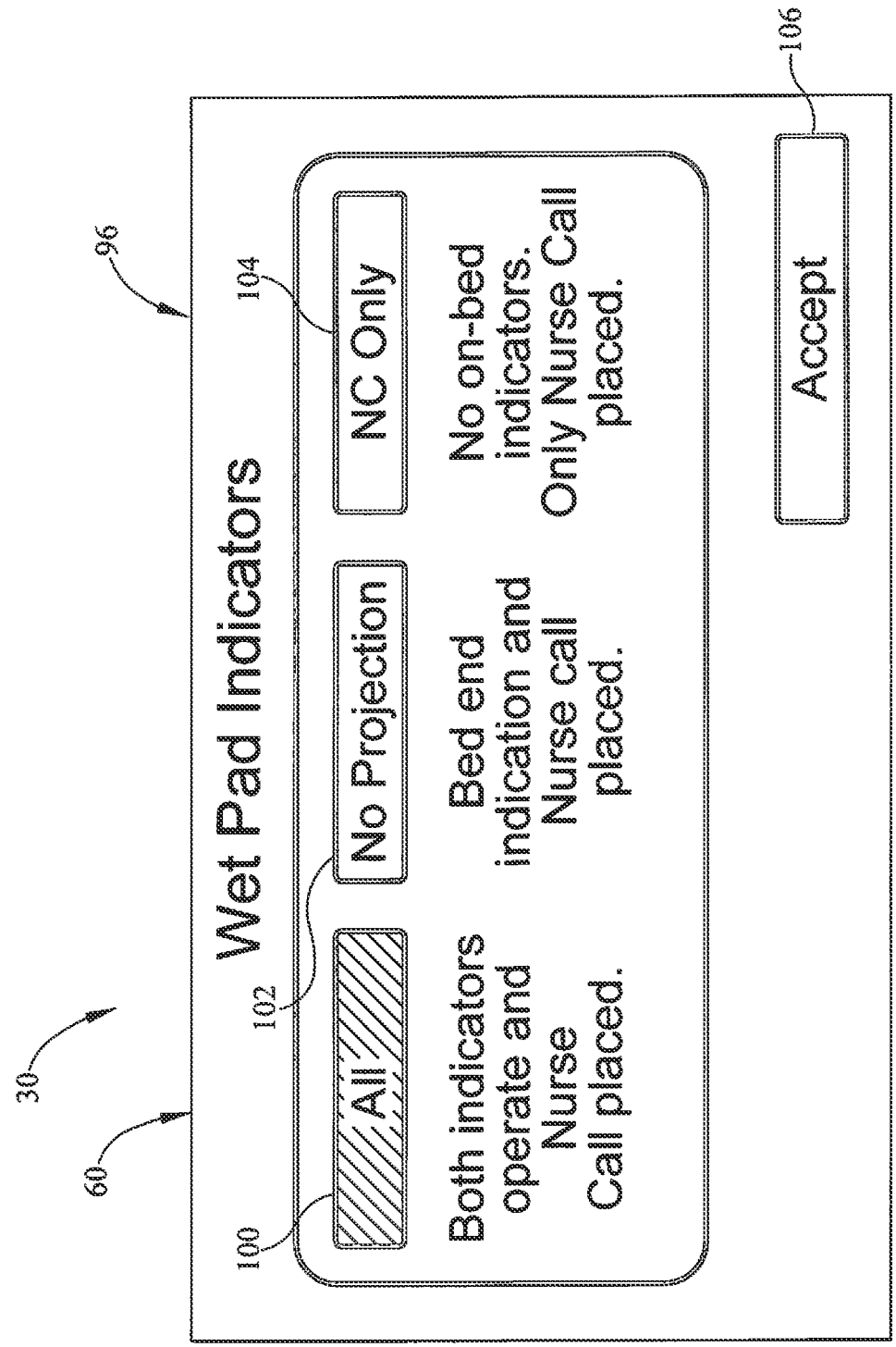
Figure 7:
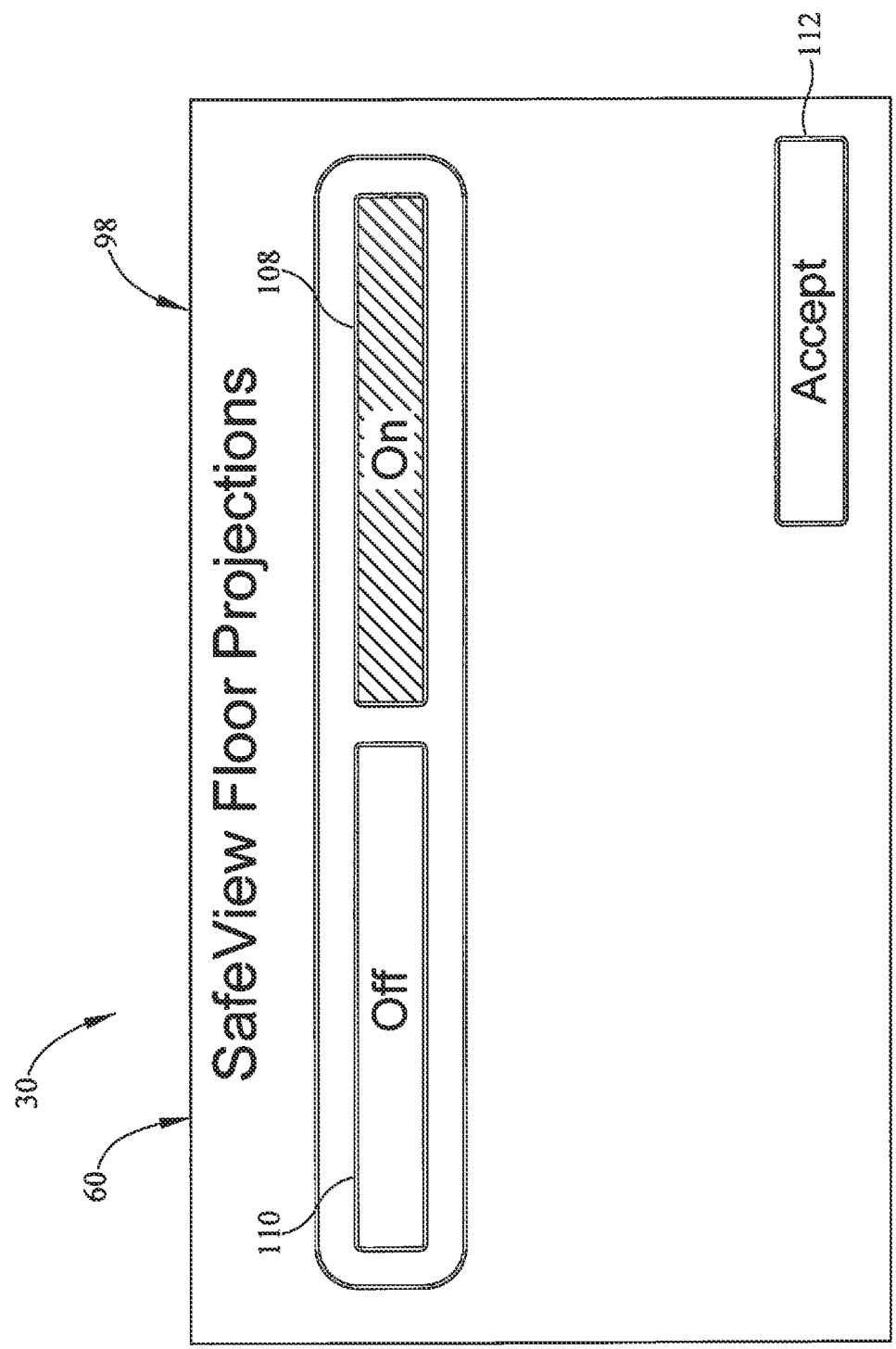

The indicator settings screen 90 includes an indicator button icon 92 and a projector button icon 94 that, when selected by a user, activate an incontinence indicator screen 96, as shown in FIG. 6, and a projection screen 98, as shown in FIG. 7. The indicator button icon 92 depicts WATCH-CARE™, which is a proprietary term that is used to represent various functions associated with the detection and notification system 16.

With the incontinence indicator screen 96 activated, the user may make a selection to alter the appearance of the first indicator 32. The incontinence indicator screen 96 includes a first indicator button icon 100, a second indicator button icon 102, and a third indicator button icon 104. The first button icon 100, when selected, programs the controller 20 to cause the first indicator 32 to display and illuminate the water droplet 56 using both the indicator panel 46 and the projector 48. The second button icon 102, when selected, programs the controller 20 to cause the first indicator to display the water droplet 56 using only the indicator panel 46. The third button icon 104, when selected, programs the controller 20 to cause the first indicator 32 to be turned off completely. Once the user is finished making a selection, an accept button icon 106 may be selected to activate the desired appearance of the first indicator 32. In the illustrative embodiment, the second indicator 34 continues to notify the caregiver regardless of the button icon selection made on the incontinence indicator screen 96; however, in other embodiments, the appearance of the notification provided at the second location by the second indicator may also be altered.

With the projection screen 98 activated, the user may make additional selections to alter the appearance of the illuminated iconic representations 52 from the projector 48 as shown in FIG. 7. The projection screen 98 includes a first projector button icon 108 that, when selected, turns the floor projections on and a second projector button icon 110 that, when selected, turns the floor projections off. Once the user is finished making a selection, an accept button icon 112 may be selected to activate the desired appearance of the illuminated iconic representations 52 from the projector 48.

Although certain illustrative embodiments have been described in detail above, variations and modifications exist within the scope and spirit of this disclosure as described and as defined in the following clauses and claims.

The invention claimed is:

1. A detection and notification system comprising a condition-responsive sensor configured to produce a signal indicative of moisture associated with a bodily fluid being present, the sensor being supported on a patient support apparatus, an external alarm system including a first indicator located in a proximate location to the sensor and a second indicator located in a remote location out of view from the sensor, the first and second indicators displaying a first iconic representation indicative of a lack of moisture and a second iconic representation indicative of the presence of moisture, and a controller coupled to the sensor and including a processor and a memory device storing instructions that, when executed, cause the first indicator to display selectively the first iconic representation or the second iconic representation when the condition-responsive sensor produces the signals and the second indicator to display the second iconic representation when the condition-responsive sensor produces the signals.

2. The detection and notification system of claim 1, wherein the first indicator includes at least one of an indicator panel for displaying the iconic representations and a projector for illuminating the iconic representations on a surface spaced apart from the projector.

3. The detection and notification system of claim 2, further comprising a user interface with a touch screen that includes a number of button icons for receiving user inputs to control the first indicator to cause the first indicator to display selectively the first iconic representation or the second iconic representation.

4. The detection and notification system of claim 3, wherein the button icons includes a first indicator button icon that, when selected, causes the first indicator to turn off such that the first and second iconic representations are displayed only by the second indicator.

5. The detection and notification system of claim 4, wherein the button icons include a second indicator button icon that, when selected, causes the indicator panel and the projector to display both the first and second iconic representations such that the first and second iconic representations are displayed by both the first the second indicators.

6. The detection and notification system of claim 5, wherein the button icons include a projector button icon that, when selected, causes the projector to turn off such that the first and second iconic representations are displayed only by the indicator panel and the second visual indicator.

7. The detection and notification system of claim 1, wherein the first visual indicator is configured to continue to display the first iconic representation when there is a presence of moisture.

8. The detection and notification system of claim 1, wherein the controller causes the first indicator to display the first iconic representation when the condition-responsive sensor produces the signal and the second indicator to display the second iconic representation when the condition-responsive sensor produces the signal.

9. The detection and notification system of claim 8, wherein the first and second iconic representations are displayed at the same time.

10. The detection and notification system of claim 1, further comprising a user interface configured to receive a user input to enable and disable the first indicator, wherein when the first indicator is disabled, no iconic representation that moisture is present is provided by the first indicator, and
wherein the user interface is configured to receive a second user input, and, in response to the second user input, the first indicator continues displaying the first iconic representation after the condition-responsive sensor determines that moisture is present.

11. A detection and notification system comprising
an incontinence detection pad having a condition-responsive sensor to produce a signal indicative of moisture being present on the incontinence detection pad,
an external alarm system including a first indicator located in a proximate location to the incontinence detection pad and a second indicator located in a remote location out of view from the incontinence detection pad, and
a controller coupled to the incontinence detection pad and including a processor and a memory device storing instructions that, when executed, cause the first indicator to display selectively a first visual indication or a second visual indication when the condition-responsive sensor produces the signal and the second indicator to display the second visual indication when the condition-responsive sensor produces the signal.

12. The detection and notification system of claim 11, wherein the first indicator displays the first visual indication when the incontinence detection pad is installed on the patient support apparatus, the second visual indication displays the first visual indication when there is a lack of moisture on the incontinence detection pad, and the second indicator displays the second visual indication when there is a presence of moisture on the incontinence detection pad while the first indicator continues displaying the first visual indication.

13. The detection and notification system of claim 11, wherein the first visual indicator is configured to continue to display the first visual indication when there is a presence of moisture on the incontinence detection pad.

14. The detection and notification system of claim 11, wherein the first indicator includes at least one of an indicator panel for displaying the visual indications and a projector for illuminating the visual indications on a surface spaced apart from the projector.

15. The detection and notification system of claim 14, further comprising a user interface with a touch screen that includes a number of button icons for receiving user inputs to control the first indicator to cause the first indicator to display selectively the first visual indication or the second visual indication.

16. The detection and notification system of claim 15, wherein the button icons includes a first indicator button icon that, when selected, causes the first indicator to turn off such that the first and second visual indications are displayed only by the second indicator.

17. The detection and notification system of claim 16, wherein the button icons include a second indicator button icon that, when selected, causes the indicator panel and the projector to display both the first and second visual indications such that the first and second visual indications are displayed by both the first the second indicators.

18. The detection and notification system of claim 17, wherein the button icons include a projector button icon that, when selected, causes the projector to turn off such that the first and second visual indications are displayed only by the indicator panel and the second visual indicator.

19. The detection and notification system of claim 11, wherein the controller causes the first indicator to display the first visual indication when the condition-responsive sensor produces the signal and the second indicator to display the second visual indication when the condition-responsive sensor produces the signal, and wherein the first and second visual indications are displayed at the same time.

20. The detection and notification system of claim 11, further comprising a user interface configured to receive a user input to enable and disable the first indicator, wherein when the first indicator is disabled, no visual indication that moisture is present on the incontinence detection pad is provided by the first indicator, and
wherein the user interface is configured to receive a second user input, and, in response to the second user input, the first indicator continues displaying the first visual indication after the condition-responsive sensor determines that moisture is present on the incontinence detection pad.

* * * * *